United States Patent
Fonseca et al.

(10) Patent No.: US 10,524,674 B2
(45) Date of Patent: Jan. 7, 2020

(54) SYSTEM AND METHOD FOR CARDIORESPIRATORY SLEEP STAGE CLASSIFICATION

(71) Applicant: KONINKLIJKE PHILIPS N.V., Eindhoven (NL)

(72) Inventors: Pedro Miguel Fonseca, Borgerhout (BE); Xi Long, Eindhoven (NL); Nicolaas Gregorius Petrus Den Teuling, Eindhoven (NL); Reinder Haakma, Eindhoven (NL); Ronaldus Maria Aarts, Geldrop (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 15/536,680

(22) PCT Filed: Dec. 10, 2015

(86) PCT No.: PCT/IB2015/059505
§ 371 (c)(1),
(2) Date: Jun. 16, 2017

(87) PCT Pub. No.: WO2016/097945
PCT Pub. Date: Jun. 23, 2016

(65) Prior Publication Data
US 2017/0360308 A1    Dec. 21, 2017

Related U.S. Application Data (60) Provisional application No. 62/093,430, filed on Dec. 18, 2014.

(51) Int. Cl.
*A61B 5/024* (2006.01)
*A61B 5/00* (2006.01)
*A61B 5/08* (2006.01)

(52) U.S. Cl.
CPC .............. *A61B 5/024* (2013.01); *A61B 5/08* (2013.01); *A61B 5/4806* (2013.01); *A61B 5/4812* (2013.01); *A61B 5/7264* (2013.01)

(58) Field of Classification Search
CPC ..... A61B 5/024; A61B 5/4812; A61B 5/4806; A61B 5/7264; A61B 5/08; G06F 19/00
See application file for complete search history.

(56) References Cited

U.S. PATENT DOCUMENTS

| 5,732,696 A * | 3/1998 | Rapoport | A61B 5/0476 600/301 |
| 7,509,163 B1 * | 3/2009 | Luo | A61B 5/0476 600/544 |

(Continued)

FOREIGN PATENT DOCUMENTS

| WO | 2006054306 A2 | 5/2006 |
| WO | 2014118693 A1 | 8/2014 |

OTHER PUBLICATIONS

Devot, S., R. Dratwa, and E. Naujokat. Sleep/wake detection based on cardiorespiratory signals and actigraphy. In: Proc. 2010 Annu. Int. Conf. IEEE Eng. Med. Biol. Soc., 2010.

(Continued)

*Primary Examiner* — Catherine M Voorhees (57) ABSTRACT

The present disclosure pertains to a system configured to determine one or more parameters based on cardiorespiratory information from a subject and determine sleep stage classifications based on a discriminative undirected probabilistic graphical model such as Conditional Random Fields using the determined parameters. The system is advantageous because sleep is a structured process in which parameters determined for individual epochs are not independent over time and the system determines the sleep stage classifications based on parameters determined for a current epoch, determined relationships between parameters, sleep stage classifications determined for previous epochs, and/or other information. The system does not assume that determined parameters are discriminative during an entire sleep stage, but maybe indicative of a sleep stage transition alone.

(Continued)

In some embodiments, the system comprises one or more sensors, one or more physical computer processors, electronic storage, and a user interface.

15 Claims, 7 Drawing Sheets

(56) References Cited

U.S. PATENT DOCUMENTS

| | | | |
|---|---|---|---|
| 7,894,890 B2* | 2/2011 | Sun | A61N 1/36135 600/544 |
| 8,562,526 B2 | 10/2013 | Heneghan et al. | |
| 2005/0267362 A1* | 12/2005 | Mietus | A61B 5/0205 600/429 |
| 2006/0111635 A1* | 5/2006 | Todros | A61B 5/0402 600/484 |
| 2009/0203972 A1* | 8/2009 | Heneghan | A61B 5/0507 600/301 |
| 2011/0034811 A1 | 2/2011 | Naujokat et al. | |

OTHER PUBLICATIONS

F. Jurysta, P. van de Borne, P. F. Migeotte, M. Dumont, J. P. Lanquart, J. P. Degaute, and P. Linkowski, "A study of the dynamic interactions between sleep EEG and heart rate variability in healthy young men," Clin. Neurophysiol., vol. 114, No. 11, pp. 2146-2155, Nov. 2003.

Kortelainen, J. M., M. O. Mendez, A. M. Bianchi, M. Matteucci, and S. Cerutti. Sleep staging based on signals acquired through bed sensor. IEEE Trans. Inf. Technol. Biomed. 14:776-785, 2010.

Lafferty, J., A. Mccallum, and F. C. N. Pereira. Conditional random fields: Probabilistic models for segmenting and labeling sequence data. In: Proc. 18th Int. Conf. Mach. Learn., 2001.

Long, X., P. Fonseca, J. Foussier, R. Haakma, and R. Aarts. Sleep and Wake Classification with Actigraphy and Respiratory Effort Using Dynamic Warping. IEEE J. Biomed. Heal. informatics , 2013.

Willemen, T., D. Van Deun, V. Verhaert, M. Vandekerckhove, V. Exadaktylos, J. Verbraecken, S. Van Huffel, B. Haex, and J. Vander Sloten. An evaluation of cardio-respiratory and movement features with respect to sleep stage classification. IEEE J. Biomed. Heal. informatics , 2013.

* cited by examiner

SYSTEM AND METHOD FOR CARDIORESPIRATORY SLEEP STAGE CLASSIFICATION

CROSS-REFERENCE TO PRIOR APPLICATIONS

This application is the U.S. National Phase application under 35 U.S.C. § 371 of International Application Serial No. PCT/IB2015/059505, filed on 10 Dec. 2015, which claims the benefit of U.S. Application Ser. No. 62/093,430, filed on 18 Dec. 2014. These applications are hereby incorporated by reference herein.

BACKGROUND

1. Field

The present disclosure pertains to a system and method for determining sleep stage indicators in a subject for individual epochs of time during a sleep session.

2. Description of the Related Art

Assessment of sleep quality based on monitoring sleep and wake phases during bedtime is known. Over-night electroencephalography (EEG) recordings with manually scored hypnograms (done by sleep technicians) for analysis of sleep architecture and occurrence of specific sleep-related problems are known. Manual sleep staging is a time-consuming task that requires the help of a sleep technician. Sensors used during overnight EEG are disruptive of sleep and often require care to apply correctly (e.g., requiring the help of the sleep technician). Typical systems facilitate sleep stage determination for a current epoch of time within a sleep session based on information determined for only that current epoch of time. Typical systems do not take into account information determined for previous epochs when facilitating determination of the sleep stage for the current epoch.

SUMMARY

Accordingly, one or more aspects of the present disclosure relate to a system configured to determine sleep stage indicators in a subject for individual epochs of time during a sleep session. The system comprises one or more sensors, one or more physical computer processors, and/or other components. The one or more sensors are configured to generate output signals conveying information related to cardiorespiratory activity of the subject. The one or more physical computer processors are configured by computer readable instructions to: determine one or more cardiorespiratory activity parameters of the subject based on the output signals by (a) determining a first cardiorespiratory activity parameter and a second cardiorespiratory activity parameter for a first epoch of time and (b) determining the first cardiorespiratory activity parameter and the second cardiorespiratory activity parameter for a second epoch of time; determine one or more relationships between the one or more cardiorespiratory activity parameters of the subject by determining a relationship between the first cardiorespiratory activity parameter and the second cardiorespiratory activity parameter for multiple individual epochs of time; and determine sleep stage indicators that indicate a sleep stage of the subject for the individual epochs of time based on the one or more determined relationships and the one or more determined parameters. The one or more physical computer processors are configured to determine the sleep stage indicators such that: a first sleep stage indicator for the first epoch of time is determined based on the first cardiorespiratory activity parameter and the second cardiorespiratory activity parameter determined for the first epoch of time and the relationship between the first cardiorespiratory activity parameter and the second cardiorespiratory activity parameter over multiple individual epochs of time; and a second sleep stage indicator for the second epoch of time is determined based on the first cardiorespiratory activity parameter and the second cardiorespiratory activity parameter determined for the second epoch of time, the relationship between the first cardiorespiratory activity parameter and the second cardiorespiratory activity parameter over multiple individual epochs of time, and the first sleep stage indicator.

Another aspect of the present disclosure relates to a method for determining sleep stage indicators in a subject for individual epochs of time during a sleep session with a determination system. The determination system comprises one or more sensors, one or more physical computer processors, and/or other components. The method comprises: generating, with the one or more sensors, output signals conveying information related to cardiorespiratory activity of the subject; determining, with the one or more physical computer processors, one or more cardiorespiratory activity parameters of the subject based on the output signals by (a) determining a first cardiorespiratory activity parameter and a second cardiorespiratory activity parameter for a first epoch of time and (b) determining the first cardiorespiratory activity parameter and the second cardiorespiratory activity parameter for a second epoch of time; determining, with the one or more physical computer processors, one or more relationships between the one or more cardiorespiratory activity parameters of the subject by determining a relationship between the first cardiorespiratory activity parameter and the second cardiorespiratory activity parameter for multiple individual epochs of time; and determining, with the one or more physical computer processors, sleep stage indicators that indicate a sleep stage of the subject for the individual epochs of time based on the one or more determined relationships and the one or more determined parameters such that a first sleep stage indicator for the first epoch of time is determined based on the first cardiorespiratory activity parameter and the second cardiorespiratory activity parameter determined for the first epoch of time and the relationship between the first cardiorespiratory activity parameter and the second cardiorespiratory activity parameter over multiple individual epochs of time, and a second sleep stage indicator for the second epoch of time is determined based on the first cardiorespiratory activity parameter and the second cardiorespiratory activity parameter determined for the second epoch of time, the relationship between the first cardiorespiratory activity parameter and the second cardiorespiratory activity parameter over multiple individual epochs of time, and the first sleep stage indicator.

Still another aspect of the present disclosure relates to a system configured to determine sleep stage indicators in a subject for individual epochs of time during a sleep session. The system comprises means for generating output signals conveying information related to cardiorespiratory activity of the subject; means for determining one or more cardiorespiratory activity parameters of the subject based on the output signals by (a) determining a first cardiorespiratory activity parameter and a second cardiorespiratory activity parameter for a first epoch of time and (b) determining the first cardiorespiratory activity parameter and the second cardiorespiratory activity parameter for a second epoch of time; means for determining one or more relationships between the one or more cardiorespiratory activity parameters of the subject by determining a relationship between the first cardiorespiratory activity parameter and the second cardiorespiratory activity parameter for multiple individual epochs of time; and means for determining sleep stage indicators that indicate a sleep stage of the subject for the individual epochs of time based on the one or more determined relationships and the one or more determined parameters such that: a first sleep stage indicator for the first epoch of time is determined based on the first cardiorespiratory activity parameter and the second cardiorespiratory activity parameter determined for the first epoch of time and the relationship between the first cardiorespiratory activity parameter and the second cardiorespiratory activity parameter over multiple individual epochs of time; and a second sleep stage indicator for the second epoch of time is determined based on the first cardiorespiratory activity parameter and the second cardiorespiratory activity parameter determined for the second epoch of time, the relationship between the first cardiorespiratory activity parameter and the second cardiorespiratory activity parameter over multiple individual epochs of time, and the first sleep stage indicator.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
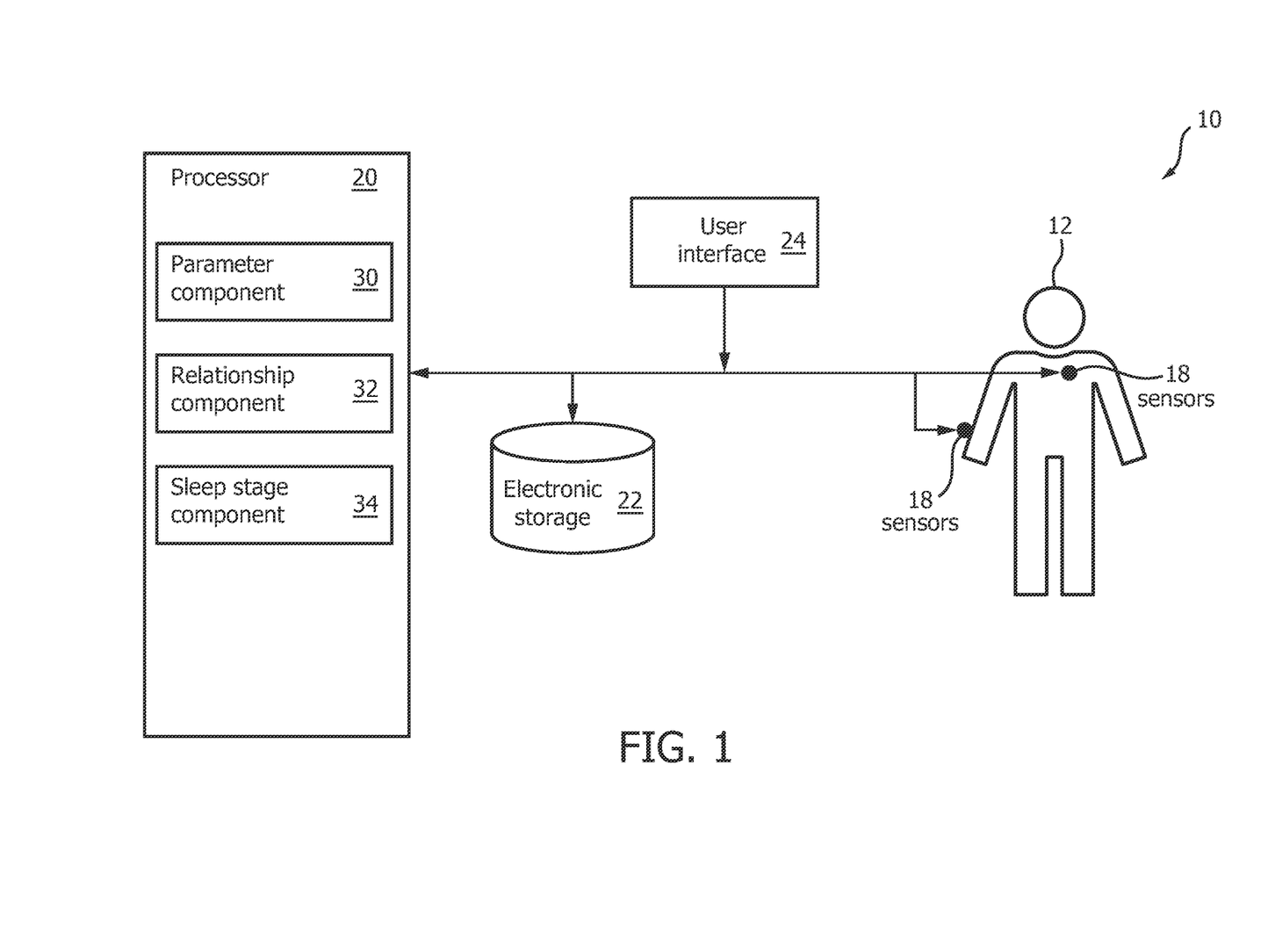
FIG. 1 illustrates a system configured to determine sleep stage indicators in a subject for individual epochs of time during a sleep session.

FIG. 1 illustrates a system 10 configured to determine sleep stage indicators in a subject 12 for individual epochs of time during a sleep session. The sleep stage indicators may correspond to and/or be the same as sleep stage classifications. The sleep stage indicators and/or classifications may be associated with rapid eye movement (REM) sleep, non-rapid eye movement (NREM) sleep (e.g., including stage N3 sleep), and/or other sleep in subject 12. System 10 is configured to determine the sleep stage indicators based on cardiorespiratory information (e.g., information related to cardiac activity, respiratory activity, and/or movement) from subject 12 and/or other information. The cardiorespiratory information may be indicative of and/or correspond to cardiorespiratory activity in subject 12. Cardiorespiratory information provides a promising alternative and/or compliment to EEG information because cardiorespiratory information may be measured using unobtrusive methods and/or sensors (described below). System 10 is configured to perform cardiorespiratory information based determination of the sleep stage indicators based on information from unobtrusive sensors that generate output signals that convey information related to cardiac activity, respiratory activity, body movements and/or other characteristics of subject 12.

System 10 is configured to determine one or more parameters based on the cardiorespiratory information and determine the sleep stage indicators (and/or sleep stage classifications) based on a discriminative undirected probabilistic graphical model such as Conditional Random Fields (e.g., a Linear-Chain Conditional Random Fields (CRF) classifier) using the determined parameters. The one or more parameters may be and/or include one or more features extracted from the information related to cardiorespiratory activity of the subject conveyed by output signals generated by the unobtrusive sensors. Conditional Random Fields is a generalization of a Hidden Markov Model that conditions the discriminative undirected probabilistic graphical model based on previous sleep (e.g., previous sleep sessions and/or previous sleep during a current sleep session) of subject 12. System 10 is advantageous because sleep is a structured process in which parameters determined for individual epochs are not independent over time and system 10 determines the sleep stage indicators (and/or sleep stage classifications) based on parameters determined for a current epoch, determined relationships between parameters, sleep stage indicators and/or classifications determined for previous epochs, and/or other information. In some embodiments, system 10 determines a sleep stage indicator for a current epoch based on parameters determined for one or more previous epochs (e.g., in addition to the parameters determined for the current epoch, determined relationships between parameters, and sleep stage indicators and/or classifications determined for previous epochs). System 10 does not assume that determined parameters are discriminative during an entire sleep stage, but may be indicative of a sleep stage transition alone. In some embodiments, system 10 comprises one or more sensors 18, one or more physical computer processors 20, electronic storage 22, a user interface 24, and/or other components.

Sensors 18 are configured to generate output signals conveying information related to cardiorespiratory activity in subject 12. The cardiorespiratory activity of subject 12 may correspond to a sleep stage of subject 12 and/or other characteristics of subject 12. The sleep stage of subject 12 may be associated with rapid eye movement (REM) sleep, non-rapid eye movement (NREM) sleep, and/or other sleep. Sensors 18 may comprise one or more sensors that generate output signals that convey information related to cardiorespiratory activity in subject 12 directly and/or indirectly. For example, one or more sensors 18 may generate an output based on a heart rate of subject 12 (e.g., sensors 18 may be and/or include a heart rate sensor located on the chest of subject 12, and/or be configured as a bracelet on a wrist of subject 12, and/or be located on another limb of subject 12), movement of subject 12 (e.g., sensors 18 may include a bracelet around the wrist and/or ankle of subject 12 with an accelerometer such that sleep may be analyzed using actigraphy signals), respiration of subject 12, and/or other characteristics of subject 12. Although sensors 18 are illustrated at two individual locations on subject 12, this is not intended to be limiting. Sensors 18 may include sensors disposed in a plurality of locations, such as for example, within (or in communication with) user interface 24, coupled (in a removable manner) with clothing of subject 12, worn by subject 12 (e.g., as a headband, wristband, etc.), positioned to point at subject 12 while subject 12 sleeps (e.g., a camera that conveys output signals related to movement of subject 12), and/or in other locations.

Processor 20 is configured to provide information processing capabilities in system 10. As such, processor 20 may comprise one or more of a digital processor, an analog processor, a digital circuit designed to process information, an analog circuit designed to process information, a state machine, and/or other mechanisms for electronically processing information. Although processor 20 is shown in FIG. 1 as a single entity, this is for illustrative purposes only. In some embodiments, processor 20 may comprise a plurality of processing units. These processing units may be physically located within the same device, or processor 20 may represent processing functionality of a plurality of devices operating in coordination.

As shown in FIG. 1, processor 20 is configured to execute one or more computer program components. The one or more computer program components may comprise one or more of a parameter component 30, a relationship component 32, a sleep stage component 34, and/or other components. Processor 20 may be configured to execute components 30, 32, and/or 34 by software; hardware; firmware; some combination of software, hardware, and/or firmware; and/or other mechanisms for configuring processing capabilities on processor 20.

It should be appreciated that although components 30, 32, and 34 are illustrated in FIG. 1 as being co-located within a single processing unit, in embodiments in which processor 20 comprises multiple processing units, one or more of components 30, 32, and/or 34 may be located remotely from the other components. The description of the functionality provided by the different components 30, 32, and/or 34 described below is for illustrative purposes, and is not intended to be limiting, as any of components 30, 32, and/or 34 may provide more or less functionality than is described. For example, one or more of components 30, 32, and/or 34 may be eliminated, and some or all of its functionality may be provided by other components 30, 32, and/or 34. As another example, processor 20 may be configured to execute one or more additional components that may perform some or all of the functionality attributed below to one of components 30, 32, and/or 34.

Parameter component 30 is configured to determine one or more cardiorespiratory activity parameters of subject 12. The one or more cardiorespiratory activity parameters of subject 12 are determined based on the output signals from sensors 18, information entered and/or received via user interface 24, information stored in electronic storage 22, and/or other information. In some embodiments, the parameters may be and/or include features extracted from the information conveyed by the output signals from sensors 18. For example, in some embodiments, a parameter may be an extracted feature by itself. In some embodiments, a parameter may be a feature that has been mathematically and/or otherwise transformed in some way (e.g., an average, a feature that has been combined with another feature, etc.) In some embodiments, determining one or more cardiorespiratory activity parameters includes determining (e.g., extracting) one or more parameters (e.g., features) for the whole sleep session, determining one or more parameters for one or more individual epochs of time in the sleep session, and/or determining other parameters. For example, determining one or more cardiorespiratory activity parameters may include determining a first cardiorespiratory activity parameter and a second cardiorespiratory activity parameter for a first epoch of time and determining the first cardiorespiratory activity parameter and the second cardiorespiratory activity parameter again for a second epoch of time (and/or any number of epochs of time).

In some embodiments, the one or more cardiorespiratory activity parameters (e.g., features) include cardiac activity parameters, respiratory parameters, cardiorespiratory coupling parameters, and/or other parameters. In some embodiments, the cardiac activity parameters include parameters related to and/or determined based on an electrocardiogram of subject 12, and/or other parameters. In some embodiments, the cardiac activity parameters may include parameters determined based on statistics computed over R-R intervals, such as the number of intervals per epoch (e.g., expressing the average heart rate in that epoch), the nth percentile, the standard deviation and/or the range of the interval lengths, and/or other parameters. In some embodiments, the cardiac activity parameters include features derived from the frequency domain of the cardiac activity using power spectral analysis; e.g. mean spectral power, spectral entropy (a measure of irregularity), peak power, and peak frequency (frequency corresponding to the peak power). Other features capture the regularity or complexity of the cardiac activity on shorter or longer time scales.

In some embodiments, the respiration parameters (e.g., features) may include parameters indicative of respiratory effort in subject 12, a respiration rate of subject 12, a flow rate (e.g., of gas into and out of subject 12 during respiration), a volume (e.g., a tidal volume of inhaled and/or exhaled gas), a pressure (e.g., an inhalation pressure, an exhalation pressure), an amplitude (e.g., of pressure and/or any other parameter of inhaled and/or exhaled gas), and/or other parameters. In some embodiments, the respiration parameters may include a parameter indicative of variation in the respiration rate of subject 12 (and/or variation of any respiration parameter) over several epochs.

Parameter component 30 is configured such that cardiorespiratory coupling parameters (e.g., features) express a strength of a coupling between the cardiac and the respiratory autonomic systems of subject 12. The strength of this link depends on the sleep stage of subject 12. Cardiorespiratory coupling parameters may describe a phase synchronization between R-R intervals and a respiratory phase (e.g., inhalation/exhalation) of subject 12 during a number of breathing cycles. For example, cardiorespiratory coupling parameters may include a percentage of phase-synchronized periods, a ratio between the number of heart beats to breathing cycles, and/or other parameters.

In some embodiments, parameter component 30 is configured such that the parameters (e.g., features) may be determined based on a power spectral density (PSD) analysis of the output signals and/or other information. For example, parameter component 30 may be configured to compute the PSD analysis over three different frequency bands: very low frequency (VLF), 0.005-0.04 Hz, low frequency (LF), 0.04-0.15 Hz, and high frequency (HF), 0.15-0.45 Hz, from the modulus and the phase of the pole in the high frequency band, and/or from other information. Parameter component 30 is configured such that one or more of the determined parameters describe the regularity of one or more of the output signals over different time scales. For example, detrended fluctuation analysis (DFA) may be performed by parameter component 30 to identify longer-term correlations in the signal, and sample entropy to quantify the self-similarity of the signal over a given time period.

Relationship component 32 is configured to determine one or more relationships between the one or more cardiorespiratory activity parameters of subject 12. The determined relationships may be determined for an individual epoch of time, for multiple individual epochs of time (e.g., a single determined relationship holds true over multiple individual epochs of time), and/or other periods of time. Relationships may include dependencies of one parameter on another, dependencies of parameters on each other, correlations between parameters, dependencies and/or correlations between specific levels of specific parameters, trends in parameters over time, and/or other relationships. For example, as subject 12's respiration rate increases, subject 12's heart rate may increase in a corresponding manner. The strength of this coupling increases as subject 12 enters slow wave sleep and decreases as subject 12 enters REM sleep. Relationship component 32 may determine and/or identify such relationships in subject 12.

Sleep stage component 34 is configured to determine sleep stage indicators that indicate a sleep stage of subject 12 for the individual epochs of time. In some embodiments, the sleep stage indicators are probability indicators that indicate a probability of subject 12 being in one or more possible sleep stages for an individual epoch of time. In some embodiments, the sleep stage indicators are sleep stage classifications. The sleep stage indicators are determined based on the one or more determined relationships, the one or more determined parameters, the output signals, previously determined sleep stage indicators, and/or other information. The sleep stage indicators are determined based on the one or more determined relationships, the one or more determined parameters, the output signals, and/or other information for a current epoch of time and/or one or more determined relationships, determined sleep state indicators and/or classifications, and/or other information for one or more epochs of time previous to the current epoch. In some embodiments, the sleep stage indicators may be determined based on cardiorespiratory activity parameters determined for previous epochs, but this is not required. Sleep stage component 34 is configured to determine sleep stage indicators based on such (previously determined) information (e.g., relationships, sleep stage indicator, optionally parameters) because sleep is a structured process in which parameters determined for individual epochs are not independent over time (e.g., the probability that subject 12 is in N3 sleep during a current epoch is higher if subject 12 was in stage N3 sleep during the immediately previous epoch and lower if subject 12 was in REM sleep during the previous epoch).

Continuing with the example above, the sleep stage indicators are determined such that a first sleep stage indicator for the first epoch of time is determined based on the first cardiorespiratory activity parameter and the second cardiorespiratory activity parameter determined for the first epoch of time and the relationship between the first cardiorespiratory activity parameter and the second cardiorespiratory activity parameter over multiple individual epochs of time. In addition, a second sleep stage indicator for the second epoch of time is determined based on the first cardiorespiratory activity parameter and the second cardiorespiratory activity parameter determined for the second epoch of time, the relationship between the first cardiorespiratory activity parameter and the second cardiorespiratory activity parameter over multiple individual epochs of time, and the first sleep stage indicator, for example. In some embodiments, the second sleep stage indicator may be determined based on the first cardiorespiratory activity parameter and the second cardiorespiratory activity parameter determined for the first epoch of time, but this is not required.

In some embodiments, the sleep stage indicators are determined based on a sleep stage indicator for an immediately previous epoch, the one or more determined relationships, the one or more determined parameters (e.g., features) for the current epoch, the output signals for the current epoch, and/or other information using (Linear-Chain) Conditional Random Fields (CRF). Conditional Random Fields are discriminative undirected probabilistic models which explore sequence and structure in data to be classified (e.g., output signals from sensors 18, parameters (features) determined by parameter component 30 that facilitate sleep stage classification, etc.). CRF is a generalization of Hidden Markov Models (HMM) that conditions the model based on the determined parameters (features), the output signals, the relationships, and/or other information. This allows for a more expressive model that can incorporate parameter (feature) dependencies (e.g., relationships determined by relationship component 32). In HMM and other generative models, the parameters are learned by maximizing a joint probability distribution $P(w,x)$, which in turn requires a distribution of observations, $P(x)$, to be modelled and/or somehow learned from the data (e.g., information conveyed by sensor output signals). Parameters are the values (also called 'weights') that define the model (e.g., similar to having an algorithm with a constant that needs to be set). The values are chosen such that the model models the data as good as possible. Observations may refer to the inputs to the model. These inputs are the features described above, derived from the sensor outputs and/or other information. An observation may refer to one or more feature values for a given epoch (e.g., x=(x1, x2, . . . )). When parameters (features) of an observed variable x are not independent, the joint distribution may be extremely difficult to model, requiring either large amounts of training data, or strong assumptions about the variables to be made. Different features can have different statistical properties/distributions. The model models these features as 'random variables'; the exact value is not defined, instead its distribution is modelled. Modeling P(x) is difficult because all variable interactions need to be modeled. Linear-Chain Conditional Random Fields avoid this problem by computing the probability P(y|x) of a possible output (e.g., a sleep stage indication of the sleep stage that is most likely, given the observations; internally this is done by computing the probability for all sleep stages and returning the sleep stage with the highest probability) $y=(y_1, y_2, \ldots, y_n)$ given an observation $x=(x_1, x_2, \ldots, x_n)$, avoiding the explicit modelling of the marginal P(x). By simplifying the modelling problem and not requiring any assumption about the independence of the parameters/features (only about the states), discriminative models make better use of correlated, interdependent parameters (features), which are common in the case of sleep stage detection using cardiorespiratory parameters (features).

It should be noted that the Linear-Chain CRF described above is just one of the many possible ways such a classifier may be used. The configuration of the CRF may be extended to higher-orders, for example, such that individual sleep stage indicators, $y_i$, determined for a current epoch of time not only depend on the sleep stage indicator (and/or other information such as parameters, output signals, and/or relationships) for the immediately previous epoch of time, $y_i-1$, but on an arbitrarily large number of previous sleep stage determinations (and/or other information such as parameters, output signals, and/or relationships), $y_j$, for a corresponding number of epochs, with j≤i−1. Additionally and/or alternatively, $P(y_i|x)$ may depend not only on the observation for the current state $x_i$, but also on the observations of previous states $(x_i-1, \ldots x_i-j)$, with j≤i−1, effectively letting the estimation of the current state class w, depend on a sequence of observations throughout time. In that sense, the first-order, single-chain (Linear-Chain) CRF described in this invention can be seen as an embodiment of a more general class of discriminative undirected probabilistic models which can be used for sleep stage classification using cardiorespiratory features.

Figure 2A:
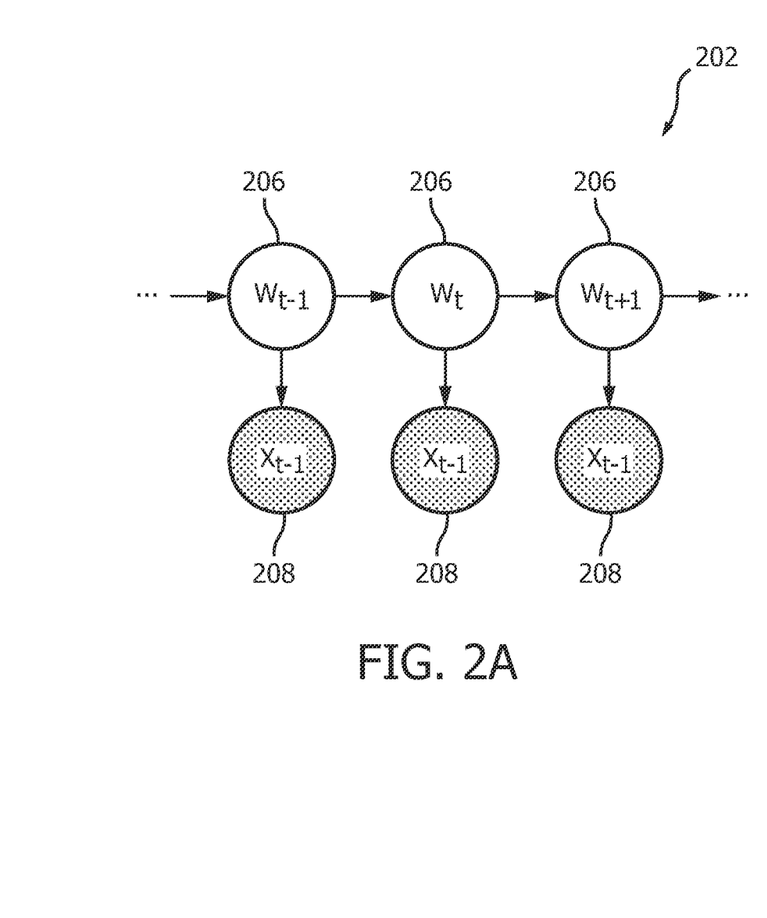
FIG. 2A illustrates a first factor graph.
Figure 2B:
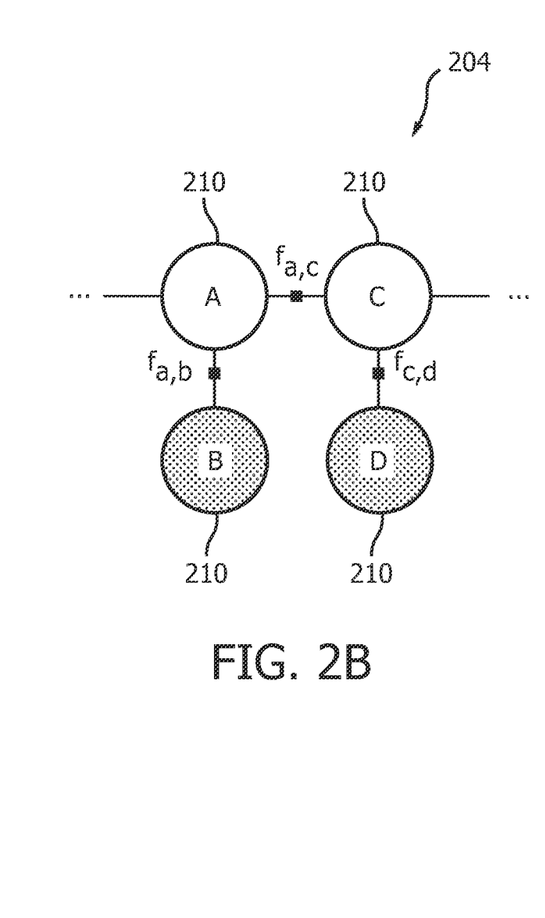
FIG. 2B illustrates a second factor graph.

FIG. 2A and FIG. 2B illustrate factor graphs 202 and 204. Parameter learning and inference in HMM is usually performed by means of factor graph 202 shown in FIG. 2A, which is a type of model that describes a probability distribution of a network using non-negative factors to express interaction between random variables. In FIG. 2A, individual states $w_t$ 206 depend on the previous individual state and observed feature vectors $x_t$ 208 depend on the individual states 206. FIG. 2B illustrates an equivalent factor graph for a subset of nodes 210. One could use FIG. 2B as a basis for the CRF model and already achieve a better performance over HMM. As a possible addition to this graph, the system is extended to include a link from node A to node D, which is how transitional features are modelled, further improving performance over HMM.

Figure 3A:
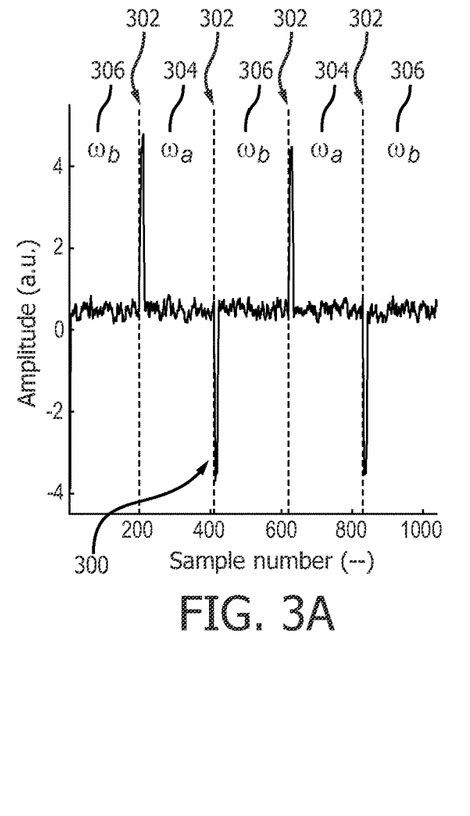
FIG. 3A illustrates an example of a parameter that is discriminative at transitions between sleep stages.
Figure 3B:
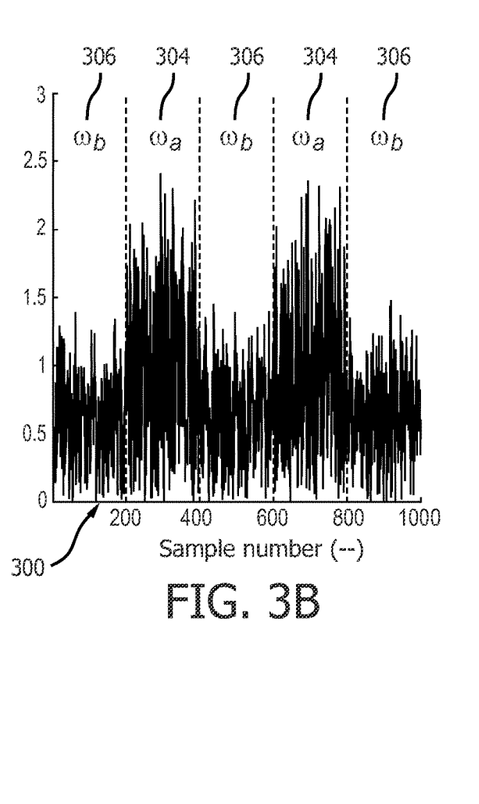
FIG. 3B illustrates the same parameter that is discriminative of the current sleep stage when using prior stage information.
Figure 3C:
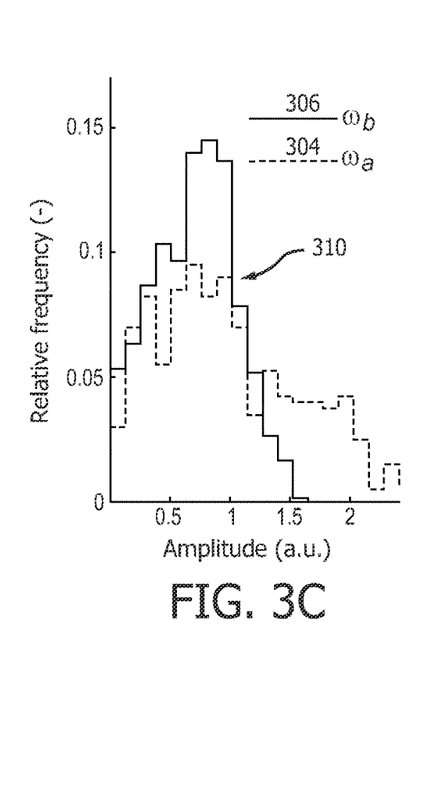
FIG. 3C is a histogram of the parameter.

In some embodiments, the sleep stage indicators indicate transitions between sleep stages in the subject. System 10 (FIG. 1) is able to indicate transitions between sleep stages because system 10 determines the sleep stage indicators (and/or sleep stage classifications) based on parameters determined for a current epoch, parameters determined for one or more previous epochs, determined relationships between parameters, sleep stage indicators and/or classifications determined for previous epochs, and/or other information. System 10 does not assume that determined parameters are discriminative during an entire sleep stage. FIGS. 3A and 3B illustrate an example of a parameter (e.g., a feature) 300 that is discriminative at the transitions 302 between sleep states $\omega_a$ 304 and $\omega_b$ 306. FIG. 3C is a histogram 310 of parameter 300. FIG. 3A illustrates an example of a feature that is discriminative at the transitions. FIG. 3B shows a different case (about why using past-state information can be important), where the feature is indicative of the current state, but only after observing multiple values. The issue with a feature like this is that there is a large overlap between the likely values for both states (as seen in the histogram of FIG. 3C).

Figure 4A:
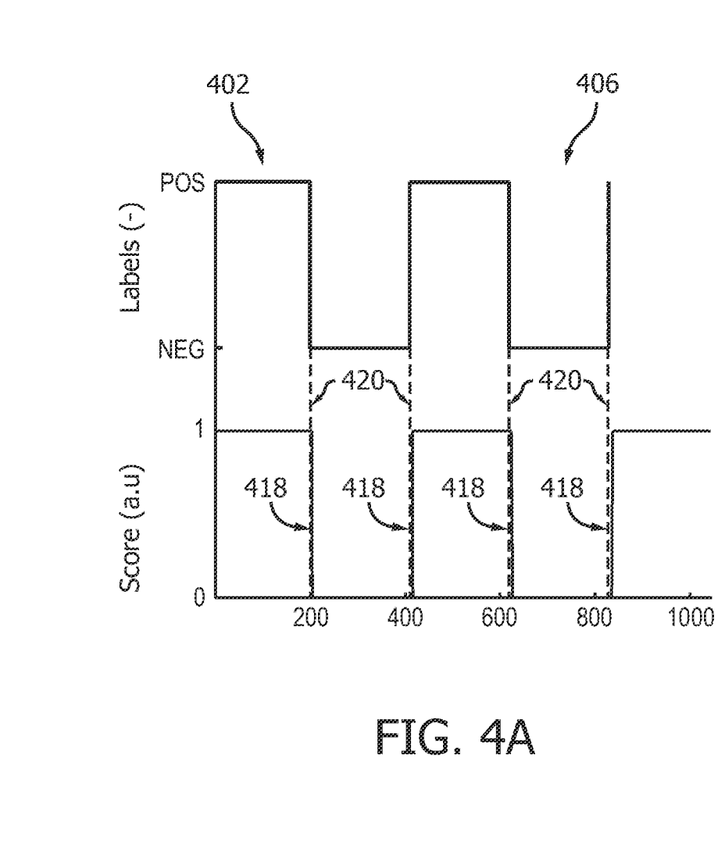
FIG. 4A illustrates posterior probability scores that indicate whether and/or how well sleep stage determinations made by the system match previously determined sleep stage annotations.
Figure 4B:
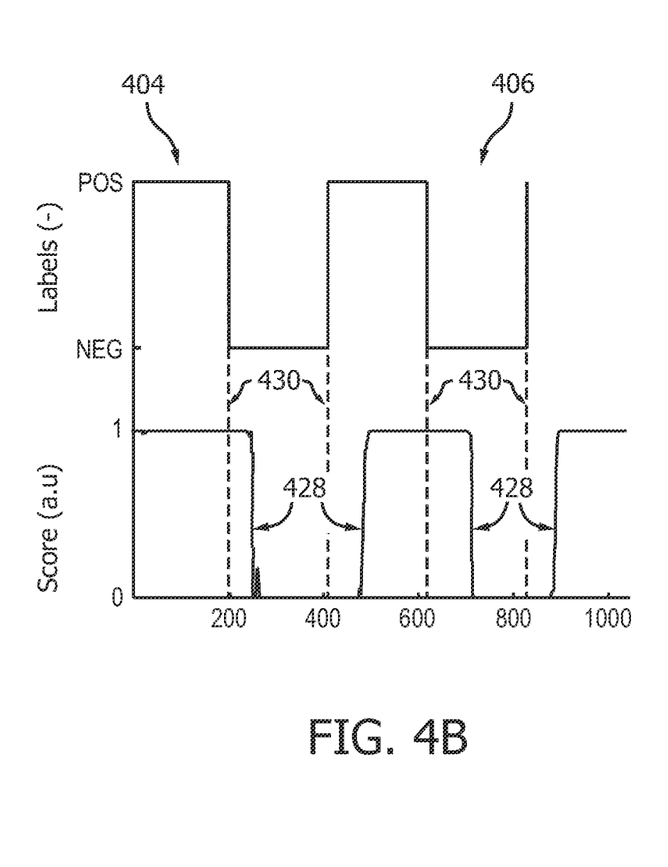
FIG. 4B illustrates posterior probability scores that indicate whether and/or how well sleep stage determinations made by another system match previously determined sleep stage annotations.

FIG. 4A illustrates posterior probability scores 402 that indicate whether and/or how well sleep stage (e.g., class) determinations made by system 10 (using the Linear-Chain CRF classifier) match previously determined sleep stage (class) annotations 406. FIG. 4B illustrates posterior probability scores 404 that indicate whether and/or how well sleep stage (e.g., class) determinations made by another system (not using the CRF classifier) match previously determined sleep stage (class) annotations. In FIGS. 4A and 4B, an annotation of 1 indicates class cob and an annotation of 0 indicates class $\omega_a$. A score closer to 1 indicates a higher posterior probability for class $\omega_b$. As illustrated in FIG. 4A (using CRF) the score obtained in the case of a parameter (e.g., a feature) indicative of sleep stage transitions matches almost perfectly with the class annotations (transitions 418 from 0 to 1 coincide with dotted lines 420). As illustrated in FIG. 4B, (not using CRF) the score obtained in the case of a parameter (e.g., a feature) indicative of sleep stage transitions does not match with the class annotations (transitions 428 from 0 to 1 do not coincide with dotted lines 430) but instead converge to the correct sleep stage (class) as more instances of unambiguous feature values are found.

Figure 5:
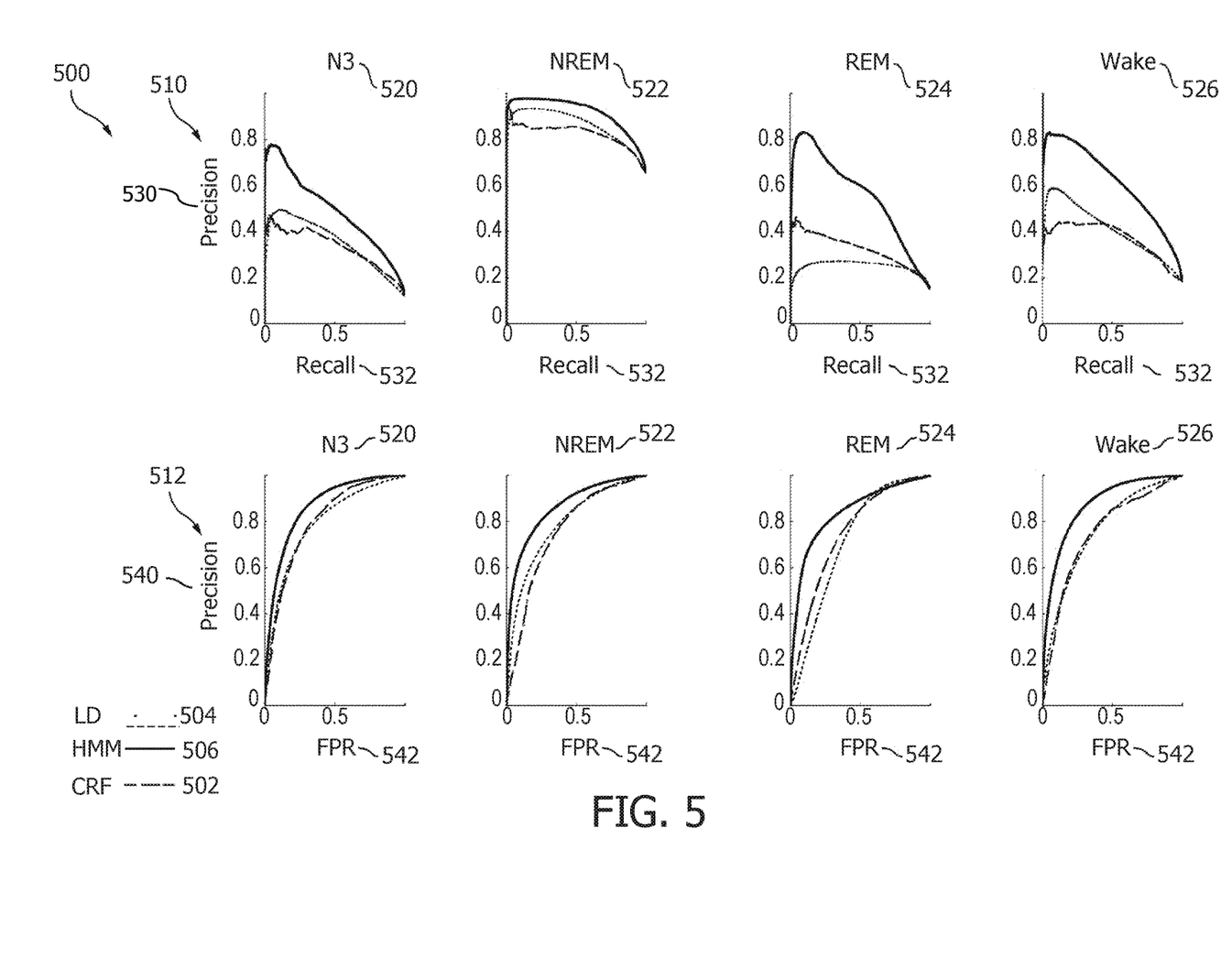
FIG. 5 illustrates results from experimentation performed using the system.
Figure 6:
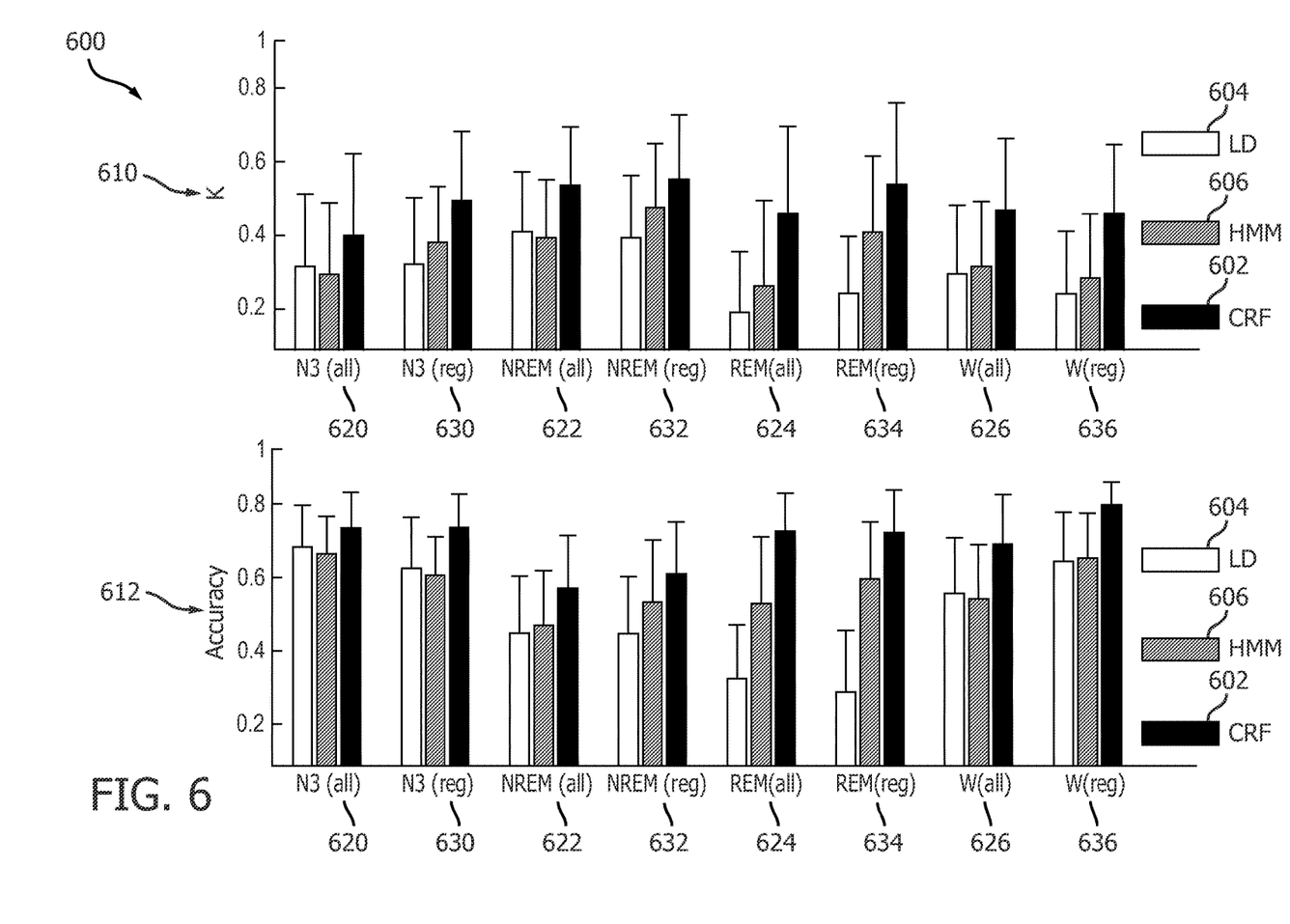
FIG. 6 illustrates additional results from experimentation performed using the system.

FIG. 5 and FIG. 6 illustrate results 500, 600 from experimentation performed using system 10 (not shown), the Conditional Random Fields classifier 502, 602, relative to other sleep stage classification systems, linear discriminants (LD) 504, 604, and Hidden Markov Models (HMM) 506, 606. The experimental dataset comprises full polysomnographic (PSG) data of 164 subjects obtained from three different databases. The first database, with two-night recordings of 149 subjects (298 recordings) was part of the database created during the EU Siesta project between 1997 and 2000 in seven different sleep laboratories. The database was restricted to subjects considered healthy (e.g., no shift workers, no depression, usual bedtime before midnight), with a Pittsburgh Sleep Quality Index 8 of at most 5. Sleep stages were scored by trained sleep technicians in five classes ('Wake', 'REM', 'S1', 'S2', 'S3', 'S4') according to the Rechtschaffen and Kales (R&K) guidelines. The second database, comprising single-night recordings of six subjects, was collected at the Philips Experience Lab of the High Tech Campus, Eindhoven, The Netherlands, during 2010 (Vitaport 3 PSG, TEMEC). The third database, comprising nine subjects, was collected at the Sleep Health Center, Boston, USA, during 2009 (Alice 5 PSG, Philips Respironics). Sleep stages for subjects in the second and third database were scored by trained sleep technicians in four classes ('Wake', 'REM', 'N1', 'N2', 'N3') according to the AASM guidelines. Although all subjects in the three databases were considered healthy, it is reasonable to expect a "first night effect". Since this is likely to have an impact in the performance of sleep stage classifiers, two separate sets were created: the first comprises all 313 recordings from the three datasets (set "all"), and the second set comprises only recordings which have a minimum percentage of each sleep stage, representative of expected regular adult sleep (at least 5% of deep sleep, 15% of REM sleep, and a sleep efficiency of at least 75%, and a minimum of 7 hours in bed) (set "regular"). This resulted in a total of 144 recordings. In order to compare the performance of the three classifiers, four detection tasks were considered: deep sleep, NREM, REM, and wake. For each of these tasks a 10-fold cross-validation scheme was used. To allow a paired comparison, the same folds were used to validate each classifier. In order to compare the classification performance of each classifier, the scores obtained for each test subject in each iteration of the cross-validation procedure were collected and aggregated (pooled). The Precision-Recall (PR) curve and the Receiver Operating Characteristic (or ROC, true positive rate (TPR) versus false positive rate (FPR)) were computed for a varying threshold on the scores output by each classifier. The threshold leading to the maximum pooled Cohen's kappa coefficient of agreement was then computed. Based on this threshold, the kappa coefficient of each subject was computed. Note that since this threshold was selected based on the pooled kappa, it will not correspond to the maximum kappa coefficient for each subject. Significance was tested with a one-tailed Wilcoxon signed-rank test for each evaluation metric.

FIG. 5 illustrates a comparison of the pooled Precision 530—Recall 532 curve 510 and ROC 512 (TPR 540 versus FPR 542) obtained with each classifier 502, 504, 506, for each detection task N3 520, NREM 522, REM 524, Wake 526 in the "all" dataset. In all detection tasks the CRF 502 classifier outperforms the other classifiers over the entire solution space.

FIG. 6 illustrates a comparison of the average kappa coefficient 610 and accuracy 612 obtained with each classifier 602, 604, 606 for the different classification tasks N3 (all) 620, N3 (reg) 630, NREM (all) 622, NREM (reg) 632, REM (all) 624, REM (reg) 634, Wake (all) 626, Wake (reg) 636 in both datasets. The performance of the CRF 602 classifier is significantly higher than both the HMM 606 and the LD 604 classifiers in all tasks 620, 622, 624, 626, 630, 632, 634, 636. The performance in the "regular" (reg) dataset is also higher than in the "all" (all) dataset, reflecting the more regular sleep structure of those subjects.

Returning to FIG. 1, electronic storage 22 comprises electronic storage media that electronically stores information. The electronic storage media of electronic storage 22 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 22 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), and/or other electronically readable storage media. Electronic storage 22 may store software algorithms (e.g., information related to CRF), information determined by processor 20, information received via user interface 24 and/or external computing systems, and/or other information that enables system 10 to function properly. Electronic storage 22 may be (in whole or in part) a separate component within system 10, or electronic storage 22 may be provided (in whole or in part) integrally with one or more other components of system 10 (e.g., processor 20).

User interface 24 is configured to provide an interface between system 10 and subject 12, and/or other users through which subject 12 and/or other users may provide information to and receive information from system 10. This enables data, cues, results, and/or instructions and any other communicable items, collectively referred to as "information," to be communicated between a user (e.g., subject 12) and one or more of sensors 18, processor 20, and/or other components of system 10. Examples of interface devices suitable for inclusion in user interface 24 comprise a keypad, buttons, switches, a keyboard, knobs, levers, a display screen, a touch screen, speakers, a microphone, an indicator light, an audible alarm, a printer, a tactile feedback device, and/or other interface devices. In some embodiments, user interface 24 comprises a plurality of separate interfaces. In some embodiments, user interface 24 comprises at least one interface that is provided integrally with processor 20 and/or other components of system 10.

It is to be understood that other communication techniques, either hard-wired or wireless, are also contemplated by the present disclosure as user interface 24. For example, the present disclosure contemplates that user interface 24 may be integrated with a removable storage interface provided by electronic storage 22. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 24 comprise, but are not limited to, an RS-232 port, RF link, an IR link, modem (telephone, cable or other). In short, any technique for communicating information with system 10 is contemplated by the present disclosure as user interface 24.

Figure 7:
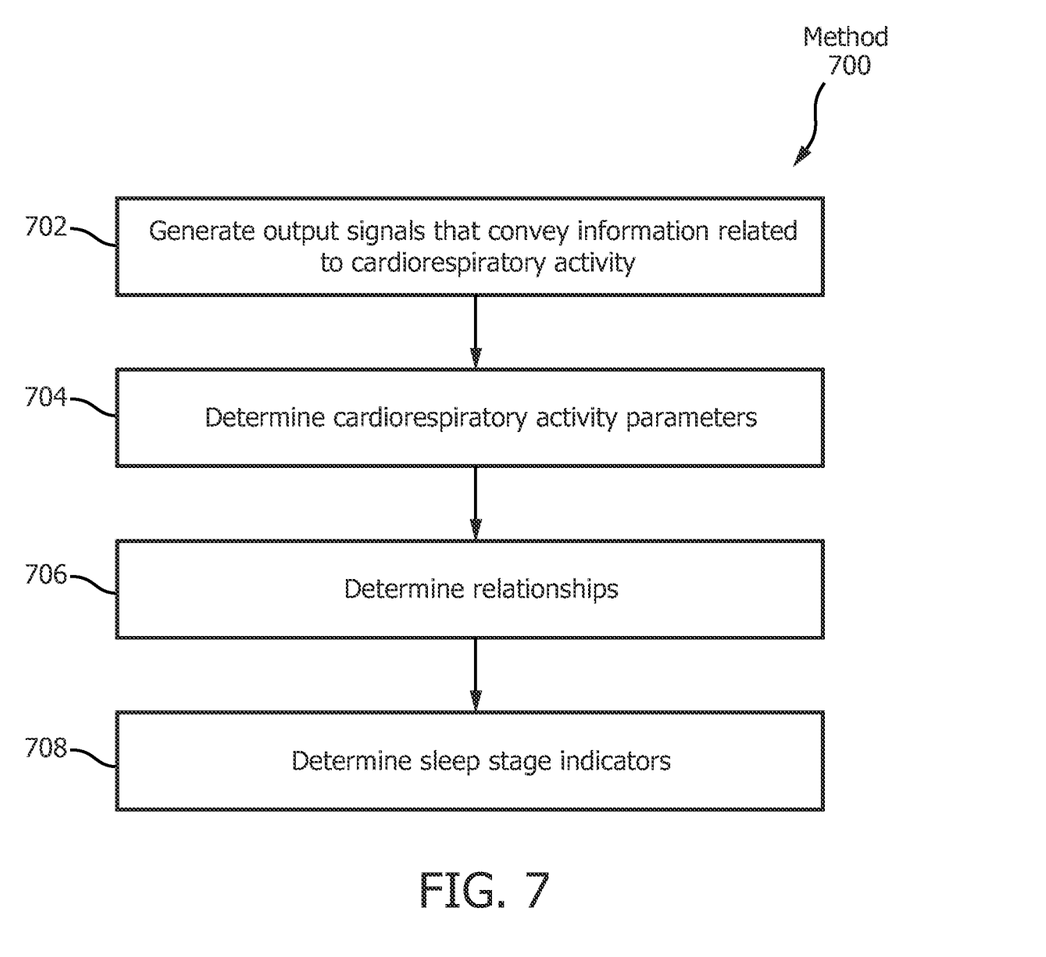
FIG. 7 illustrates a method for determining sleep stage indicators in a subject for individual epochs of time during a sleep session.

FIG. 7 illustrates a method 700 for determining sleep stage indicators in a subject for individual epochs of time during a sleep session with a determination system. The determination system comprises one or more sensors, one or more physical computer processors, and/or other components. The one or more physical computer processors are configured to execute computer program components. The computer program components comprise a parameter component, a relationship component, a sleep stage component, and/or other components. The operations of method 700 presented below are intended to be illustrative. In some embodiments, method 700 may be accomplished with one or more additional operations not described, and/or without one or more of the operations discussed. Additionally, the order in which the operations of method 700 are illustrated in FIG. 7 and described below is not intended to be limiting.

In some embodiments, method 700 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 700 in response to instructions stored electronically on an electronic storage medium. The one or more processing devices may include one or more devices configured through hardware, firmware, and/or software to be specifically designed for execution of one or more of the operations of method 700.

At an operation 702, output signals conveying information related to cardiorespiratory activity of the subject are generated. In some embodiments, generating output signals conveying information related to cardiorespiratory activity of the subject includes generating information related to cardiac activity of the subject, respiratory activity of the subject, and/or other physiological activity of the subject. In some embodiments, operation 702 is performed by one or more sensors the same as or similar to sensors 18 (shown in FIG. 1 and described herein).

At an operation 704, one or more cardiorespiratory activity parameters of the subject are determined. The one or more cardiorespiratory activity parameters of the subject are determined based on the output signals and/or other information. In some embodiments, for example, determining one or more cardiorespiratory activity parameters includes determining a first cardiorespiratory activity parameter and a second cardiorespiratory activity parameter for a first epoch of time and determining the first cardiorespiratory activity parameter and the second cardiorespiratory activity parameter for a second epoch of time. In some embodiments, the one or more cardiorespiratory activity parameters include one or more of a cardiac activity parameter, a respiratory parameter, a cardiorespiratory coupling parameter, and/or other parameters. In some embodiments, the parameters are and/or include features extracted from the information related to cardiorespiratory activity of the subject in the output signals generated by the sensors. In some embodiments, operation 704 is performed by a processor component the same as or similar to parameter component 30 (shown in FIG. 1 and described herein).

At an operation 706, one or more relationships between the one or more cardiorespiratory activity parameters of the subject are determined. Determining one or more relationships includes determining a relationship between the first cardiorespiratory activity parameter and the second cardiorespiratory activity parameter (and/or features), for example. The determined relationships may be determined for multiple individual epochs of time (e.g., a single determined relationship holds true over multiple individual epochs of time). In some embodiments, operation 706 is performed by a processor component the same as or similar to relationship component 32 (shown in FIG. 1 and described herein).

At an operation 708, sleep stage indicators that indicate a sleep stage of the subject for the individual epochs of time are determined. The sleep stage indicators are determined based on the one or more determined relationships, the one or more determined parameters, previously determined sleep stage indicators, and/or other information. Continuing with the example above, the sleep stage indicators are determined such that a first sleep stage indicator for the first epoch of time is determined based on the first cardiorespiratory activity parameter and the second cardiorespiratory activity parameter determined for the first epoch of time and the relationship between the first cardiorespiratory activity parameter and the second cardiorespiratory activity parameter over multiple individual epochs of time. In addition, a second sleep stage indicator for the second epoch of time is determined based on the first cardiorespiratory activity parameter and the second cardiorespiratory activity parameter determined for the second epoch of time, the relationship between the first cardiorespiratory activity parameter and the second cardiorespiratory activity parameter over multiple individual epochs of time, and the first sleep stage indicator, for example. In some embodiments, the second sleep stage indicator is determined based on the first cardiorespiratory activity parameter and the second cardiorespiratory activity parameter determined for the first epoch of time, but this is optional. In some embodiments, the sleep stage indicators are probability indicators that indicate a probability of the subject being in one or more possible sleep stages for an individual epoch of time. In some embodiments, the sleep stage indicators are determined based on one or more previously determined sleep stage indicators, the one or more determined relationships, and the one or more determined parameters using conditional random fields. In some embodiments, the sleep stage indicators indicate transitions between sleep stages in the subject. In some embodiments, operation 708 is performed by a processor component the same as or similar to sleep stage component 34 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A system configured to determine sleep stage indicators in a subject for individual epochs of time during a sleep session, the system comprising:

one or more sensors configured to generate output signals conveying information related to cardiorespiratory activity of the subject, the cardiorespiratory activity including cardiac activity and respiratory activity; and one or more physical computer processors configured by computer readable instructions to:

determine one or more cardiorespiratory activity parameters of the subject based on the output signals, the one or more cardiorespiratory activity parameters including cardiorespiratory coupling parameters, wherein the cardiorespiratory coupling parameters indicate a strength of a coupling between cardiac and respiratory automatic systems of the subject, wherein the indicated strength depends on sleep depth of the subject and increases as sleep depth increases, and wherein determining the one or more cardiorespiratory activity parameters comprises (a) determining a first cardiorespiratory activity parameter and a second cardiorespiratory activity parameter for a first epoch of time, and (b) determining the first cardiorespiratory activity parameter and the second cardiorespiratory activity parameter for a second epoch of time;

determine one or more relationships between at least two determined cardiorespiratory activity parameters of the subject, the one or more relationships including relationships between the cardiorespiratory coupling parameters, wherein determining the one or more relationships comprises determining a relationship between the first cardiorespiratory activity parameter and the second cardiorespiratory activity parameter for multiple individual epochs of time; and determine sleep stage indicators that indicate a sleep stage of the subject for the individual epochs of time based on the one or more determined relationships and the one or more determined cardiorespiratory activity parameters, the sleep stage indicators being determined based on probabilistic factor graph, wherein:

a first sleep stage indicator for the first epoch of time is determined based on the first cardiorespiratory activity parameter and the second cardiorespiratory activity parameter determined for the first epoch of time and the relationship between the first cardiorespiratory activity parameter and the second cardiorespiratory activity parameter over multiple individual epochs of time; and a second sleep stage indicator for the second epoch of time is determined based on the first cardiorespiratory activity parameter and the second cardiorespiratory activity parameter determined for the second epoch of time, the relationship between the first cardiorespiratory activity parameter and the second cardiorespiratory activity parameter over multiple individual epochs of time, and the first sleep stage indicator.

2. The system of claim 1, wherein the one or more physical computer processors are configured such that the sleep stage indicators are probability indicators that indicate a probability of the subject being in one or more possible sleep stages for an individual epoch of time.

3. The system of claim 1, wherein the sleep stage indicators are determined using conditional random fields, and wherein the probabilistic factor graph is a discriminative undirected probabilistic factor graph that describes a probability distribution of a network using non-negative factors to express interaction between random variables.

4. The system of claim 1, wherein the one or more physical computer processors are configured such that the sleep stage indicators indicate transitions between sleep stages in the subject.

5. A method for determining sleep stage indicators in a subject for individual epochs of time during a sleep session with a determination system, the system comprising one or more sensors and one or more physical computer processors, the method comprising:

generating, with the one or more sensors, output signals conveying information related to cardiorespiratory activity of the subject, the cardiorespiratory activity including cardiac activity and respiratory activity;

determining, with the one or more physical computer processors, one or more cardiorespiratory activity parameters of the subject based on the output signals, the one or more cardiorespiratory activity parameters including cardiorespiratory coupling parameters, wherein the cardiorespiratory coupling parameters indicate a strength of a coupling between cardiac and respiratory automatic systems of the subject, wherein the indicated strength depends on sleep depth of the subject and increases as sleep depth increases, and wherein determining the one or more cardiorespiratory activity parameters comprises (a) determining a first cardiorespiratory activity parameter and a second cardiorespiratory activity parameter for a first epoch of time and (b) determining the first cardiorespiratory activity parameter and the second cardiorespiratory activity parameter for a second epoch of time;

determining, with the one or more physical computer processors, one or more relationships between at least two determined cardiorespiratory activity parameters of the subject, the one or more relationships including relationships between the cardiorespiratory coupling parameters wherein determining the one or more relationships comprises determining a relationship between the first cardiorespiratory activity parameter and the second cardiorespiratory activity parameter for multiple individual epochs of time; and determining, with the one or more physical computer processors, sleep stage indicators that indicate a sleep stage of the subject for the individual epochs of time based on the one or more determined relationships and the one or more determined cardiorespiratory activity parameters, the sleep stage indicators being determined based on a probabilistic factor graph, wherein:

a first sleep stage indicator for the first epoch of time is determined based on the first cardiorespiratory activity parameter and the second cardiorespiratory activity parameter determined for the first epoch of time and the relationship between the first cardiorespiratory activity parameter and the second cardiorespiratory activity parameter over multiple individual epochs of time; and a second sleep stage indicator for the second epoch of time is determined based on the first cardiorespiratory activity parameter and the second cardiorespiratory activity parameter determined for the second epoch of time, the relationship between the first cardiorespiratory activity parameter and the second cardiorespiratory activity parameter over multiple individual epochs of time, and the first sleep stage indicator.

6. The method of claim 5, wherein the sleep stage indicators are probability indicators that indicate a probability of the subject being in one or more possible sleep stages for an individual epoch of time.

7. The method of claim 5, wherein the sleep stage indicators are determined using conditional random fields, and wherein the probabilistic factor graph is a discriminative undirected probabilistic factor graph that describes a probability distribution of a network using non-negative factors to express interaction between random variables.

8. The method of claim 5, wherein the sleep stage indicators indicate transitions between sleep stages in the subject.

9. A system configured to determine sleep stage indicators in a subject for individual epochs of time during a sleep session, the system comprising:

means for generating output signals conveying information related to cardiorespiratory activity of the subject, the cardiorespiratory activity including cardiac activity and respiratory activity;

means for determining one or more cardiorespiratory activity parameters of the subject based on the output signals, the one or more cardiorespiratory activity parameters including cardiorespiratory coupling parameters, wherein the cardiorespiratory coupling parameters indicate a strength of a coupling between cardiac and respiratory automatic systems of the subject, wherein the indicated strength depends on sleep depth of the subject and increases as sleep depth increases, and wherein determining the one or more cardiorespiratory activity parameters comprises (a) determining a first cardiorespiratory activity parameter and a second cardiorespiratory activity parameter for a first epoch of time and (b) determining the first cardiorespiratory activity parameter and the second cardiorespiratory activity parameter for a second epoch of time;

means for determining one or more relationships between at least two determined cardiorespiratory activity parameters of the subject, the one or more relationships including relationships between the cardiorespiratory coupling parameters, wherein determining the one or more relationships comprises determining a relationship between the first cardiorespiratory activity parameter and the second cardiorespiratory activity parameter for multiple individual epochs of time; and means for determining sleep stage indicators that indicate a sleep stage of the subject for the individual epochs of time based on the one or more determined relationships and the one or more determined cardiorespiratory activity parameters, the sleep stage indicators being determined based on a probabilistic factor graph, so that:

a first sleep stage indicator for the first epoch of time is determined based on the first cardiorespiratory activity parameter and the second cardiorespiratory activity parameter determined for the first epoch of time and the relationship between the first cardiorespiratory activity parameter and the second cardiorespiratory activity parameter over multiple individual epochs of time; and a second sleep stage indicator for the second epoch of time is determined based on the first cardiorespiratory activity parameter and the second cardiorespiratory activity parameter determined for the second epoch of time, the relationship between the first cardiorespiratory activity parameter and the second cardiorespiratory activity parameter over multiple individual epochs of time, and the first sleep stage indicator.

10. The system of claim 9, wherein the sleep stage indicators are probability indicators that indicate a probability of the subject being in one or more possible sleep stages for an individual epoch of time.

11. The system of claim 9, wherein the sleep stage indicators are determined using conditional random fields, and wherein the probabilistic factor graph is a discriminative undirected probabilistic factor graph that describes a probability distribution of a network using non-negative factors to express interaction between random variables.

12. The system of claim 9, wherein the sleep stage indicators indicate transitions between sleep stages in the subject.

13. The system of claim 1, wherein the one or more cardiorespiratory activity parameters further comprise a parameter that is discriminative of transitions between sleep stages, and wherein determining the sleep stage indicators is further based on the parameter that is discriminative of transitions between sleep stages.

14. The method of claim 5, wherein the one or more cardiorespiratory activity parameters further comprise a parameter that is discriminative of transitions between sleep stages, and wherein determining the sleep stage indicators is further based on the parameter that is discriminative of transitions between sleep stages.

15. The system of claim 9, wherein the one or more cardiorespiratory activity parameters further comprise a parameter that is discriminative of transitions between sleep stages, and wherein determining the sleep stage indicators is further based on the parameter that is discriminative of transitions between sleep stages.

* * * * *